United States Patent [19]

Domján et al.

[11] Patent Number: 4,485,825

[45] Date of Patent: Dec. 4, 1984

[54] INSTRUMENT FOR MEASURING POSITIONS AND DISPLACEMENTS OF JOINTS AND SPINAL COLUMN (ARTHROSPINOMETER)

[75] Inventors: László Domján; Géza Bálint; Sándor Bozsóky, all of Budapest, Hungary

[73] Assignee: Medicor Muvek, Budapest, Hungary

[21] Appl. No.: 402,339

[22] Filed: Jul. 27, 1982

[51] Int. Cl.³ .............................................. A61B 5/08
[52] U.S. Cl. .................................... 128/774; 128/782; 33/174 D; 33/352
[58] Field of Search ...................... 128/774, 781, 782; 33/174 D, 1 E, 1 N, 352

[56] References Cited

U.S. PATENT DOCUMENTS

| | | | |
|---|---|---|---|
| 1,097,925 | 5/1914 | Johnson | 33/352 |
| 1,860,259 | 5/1932 | Marshall | 33/352 |
| 2,186,677 | 1/1940 | Humphreys | 33/1 E |
| 2,461,864 | 2/1949 | Zuschlag | 33/352 X |
| 2,565,381 | 8/1951 | Leighton | 128/782 |
| 2,835,973 | 5/1958 | Schmuck | 33/1 E |
| 3,012,324 | 12/1961 | Swift | 33/1 E |
| 3,289,475 | 12/1966 | Kenyon | 33/352 X |
| 3,429,052 | 2/1969 | Hembd et al. | 33/174 D |

OTHER PUBLICATIONS

Roswell et al., Jour. of Bone and Joint Surgery, vol. 35-A, No. 3, Jul. 1953, pp. 784-785.

Primary Examiner—Kyle L. Howell
Assistant Examiner—John C. Hanley
Attorney, Agent, or Firm—Young & Thompson

[57] ABSTRACT

An instrument for measuring positions and displacements of portions of a human body, comprising a base plate and a belt or suction cup for detachably securing the base plate to a portion of a human body. A bifurcated holder is mounted on the base plate for rotation about a first axis, the bifurcated holder having a pair of arms, and a housing is pivotally carried between these arms for swinging movement about a second axis perpendicular to the first axis. A dip circle and a north-south-seeking compass are carried by this housing, the dip circle and compass being mounted on the housing for pivotal movement about a common third axis perpendicular to the second axis. The base plate has a scale thereon, and there is an indicator on the holder for indicating on the scale the degree of rotation of the holder relative to the base plate. There is also a scale for indicating the degree of rotation of the dip circle and compass relative to the housing, and this scale is rotatable relative to the housing about that common third axis.

6 Claims, 9 Drawing Figures

INSTRUMENT FOR MEASURING POSITIONS AND DISPLACEMENTS OF JOINTS AND SPINAL COLUMN (ARTHROSPINOMETER)

The invention relates to an instrument for measuring the positions and displacements of the joints and the spinal column. This instrument, called an arthrospinometer, can preferably be used in therapeutics of the organs of locomotion.

In all medical sciences dealing with the system of organs of locomotion and with the locomotor disorders, the accurate measurement of the angular displacements of joints has a prominent importance. For this purpose, a joint angle meter (goniometer) with two arms pivotedly pin-jointed to each other is most widely used. For measuring the elbow joint, for example, one of the arms of the goniometer is laid on the axial line of the forearm, the other one on that of the upper arm and the pin-joint is in alignment with the elbow joint. The relative position of the arms of the goniometer can be read off an angle calibration fixed to one of the arms.

However, it is very difficult to hold the arms and the pin joint of the goniometer in precise alignment with the axial lines of the forearm, the upper arm and the elbow joint for the purpose of measuring. The smallest inaccuracy results in greatly falsified measurements. The diseased elbow joint is often swollen or gummy, inflamed, thus, it is nearly impossible to find the actual elbow joint. As is well known among orthopaedic surgeons, the goniometer is accurate if the limits of the limbs are well defined. However, if the limiting ends of the bones are not clear because they are covered by too much soft material, the goniometer gives inaccurate data. In these cases, the skilled surgeon can establish the joint angle more accurate without the use of the goniometer.

The inconvenience of the goniometer is not only in the limited accuracy but in the fact, too, that there are joint positions and displacements which cannot be measured with the aid of it For example, the components of the movement of the shoulder-joint or the hip-joint can be measured only with great difficulties if at all.

To eliminate the inconveniences of the goniometer, a measuring instrument was developed, wherein a dip-circle (inclinometer) and a compass were unified. During measuring, the instrument is fixed on the patient by a belt like a wristwatch. The displacements in the vertical plane are measured by the dip-circle, in the horizontal plane by the compass. However, with this instrument only the angular field of displacement of the joint can be measured and not the contraction which is most important in the clinical practice. If the examined person is healthy, he can stretch his leg entirely. In this position, the instrument is set to zero. The patient flexes entirely his leg. The angle calibration is read out, the result gives the angle of flexure of the hip joint.

However, if the patient is ill and he cannot stretch his leg entirely (he has a flexure contraction of the hip-joint), the instrument cannot display the angle of the contraction. This is very disadvantageous since the patients having locomotor disorders have nearly always some kind of contraction and, furthermore, the measurement of contraction is very important for the clinical treatment and for the function of the organ.

This feature can be demonstrated by the example of a patient who can stretch his leg entirely but who can bend it only 90 degrees. His hip-joint is in far better condition than that of another patient who cannot stretch his legs entirely but only 20 degrees but who can bend them 100 degrees. In both cases, the known measuring instrument will show a displacement of 90 degrees which is the difference between 0 and 90 degrees and 20 and 110 degrees as well but the first patient is nearly healthy and the second one is ill.

Another disadvantage of the known type of instrument can be experienced if the displacement does not remain in the vertical or horizontal plane, i.e. it is a movement in space. With measurements on the shoulder-joint, for example, the upper arm not only lifts but also rotates, and the initial vertical plane of the dip-circle will not be vertical at the end of the motion. Thus, the value read off will be falsified.

The known instrument fixed to one part of a limb gives the actual angle value of the displacement of an examined joint if the other limb part is held in its place without any movement. If the displacement of the knee-joint is measured with an instrument fixed to the shin, the thigh must not alter its position during the rotation of the knee-joint. In the course of the examination as usual today, this is nearly impossible.

The greatest disadvantage of this known type of instrument is that it cannot be used for measurements on the spinal column which can be looked upon as a special type of joint. However, the backbone is the most important part of the locomotor system and, therefore, the measurement of its position and displacement is a focal question of the sciences dealing with organs of the locomotion system.

It is also well known by orthopaedic surgeons, that the actual motion of the spine can be measured only with great difficulties with the aid of physical examinations since the backbone is covered by soft parts, it has normal curvatures, and the motions are combined on various parts of the spine. The man can lean forward to 90 degrees with the motion of the hip joint only and without any motion of the spinal column. It has been found that the flexure movement of the spine can be measured most accurately with the aid of steel or plastic measuring tape. In the course of this measuring method, the change in distance of the first sacral vertebra spondyle from the seventh cervical vertebra spondyle is measured and from this is concluded the measure of bending forward of the spine.

In contrast with this known method, the following six motions should be detected separately: leaning forward (flexure), leaning backward (extension), leaning to the right, leaning to the left, rotation to the right and rotation to the left. Furthermore, the change of distance is measured with this method which depends on the measurements of the patient, i.e. it gives different values with different patients. This measuring is influenced by the natural curvatures of the spine, e.g. by the lumber lordosis, too.

Another measuring instrument for measuring on the spinal column is known in the art, the so called Dunham-type spondylometer. It is like a pair of caliper compasses and for the measurement, the base plate of the calibration provided on one caliper of the instrument is put on the sacrum, the end of the other caliper is pressed against the spinous process of the seventh cervical vertebra spondyle. The change of angle is read off the calibration at the end of the patient's leaning forward or back. Thus, only two motions can be measured from the above mentioned six motions with the aid of the Dunham-type spondylometer. In the principle of this instrument, it is presupposed that the distance between the sacrum and the seventh cervical vertebra spondyle does not change in the course of bending the spinal column. This postulation is fulfilled only with a stiff, numb spine. But a stiff spine is not capable to bending in any direction. Of course, the backbone is not stiff in reality, thus, the changing distance between the sacrum and the seventh cervical vertebra spondyle falsifies the measurement with the Dunham-type spondylometer.

Furthermore, the form of the sacrum is not the same in all patients, thus, the edge of the base plate of the Dunham-type spondylometer does not fit all sacrums.

An object of the present invention is to obviate or reduce the aforesaid deficiencies of the known measuring instruments. For this purpose, a universal instrument is provided for simple, reproducible and objective measuring of the positions and displacements of joints or of the spinal column.

The invention has as its basic idea that the displacements should be correlated not only to the body of the examined patient but also to an outer stable reference. For motions in the vertical plane, this reference is gravitation having a pull pointing to the centre of the Earth and, thus, being always vertical. For motions in the horizontal plane, this reference is the magnetic field of the Earth having the stable direction North-South. The motions in space or in planes other than the vertical or horizontal should be transformed into motions in the vertical or horizontal planes.

The instrument of this invention is distinguished from the above described known combination of dip-circle and compass in that the housing containing the dip-circle (inclinometer), the compass and the angle calibration related to both dip-circle and compass is pivotally jointed between the arms of a bifurcated holder and, the axis of rotation of the housing relative to the arms is perpendicular to the common axis of pointers of the combined dip-circle and compass. Furthermore, the bifurcated holder is pivotally jointed to the base plate. The axis of rotation between the bifurcated holder and the base plate is perpendicular to the axis of rotation between the housing and the arms of the holder as well as to the base plate.

The angle calibration in the housing may have scales on its both, i.e. outer and inner peripheries.

The axis of rotation between the arms of the bifurcated holder and the housing may be formed by axle pins fixed to the arms and pivotally jointed to the housing.

For securing the instrument on an object to be measured, e.g. on the forearm, upper arm, leg or backbone, a rubber belt may be fixed to the base plate.

For displaying the rotation of the bifurcated holder relative to the base plate, an angle calibration may be provided on the base plate.

Both angle calibrations, i.e. the one in the housing and the one on the base plate may be formed as two mirror image symmetrical semicircles having scales from 0 to 180 degrees and the semicircles may be differentiated by different colors.

For promoting the reading of the angle value of rotation of the bifurcated holder on the angle calibration provided on the base plate, a pointing edge indicating the middle plane of the bifurcated holder and related to the angle calibration may be provided.

The instrument should sit without any slip or displacement on the object during the measurement. For this purpose, a sucker can be attached to the base plate.

In a very simple embodiment, the base plate may have a central opening on its side opposite the bifurcated holder, and the central pin of the sucker can be fixed in this central opening. It is advantageous if the middle plane of the sucker is parallel to the base plate.

There can be situations when the instrument fixed on the body gets into the way of movement. For preventing this, an extension with adjustable length can be provided between the central pin of the sucker and the central opening of base plate.

The invention will be described hereinafter in greater detail with reference to the accompanying drawings. In the drawings, FIG. 1 shows a side view of an embodiment of the instrument of this invention;

Figure 1:
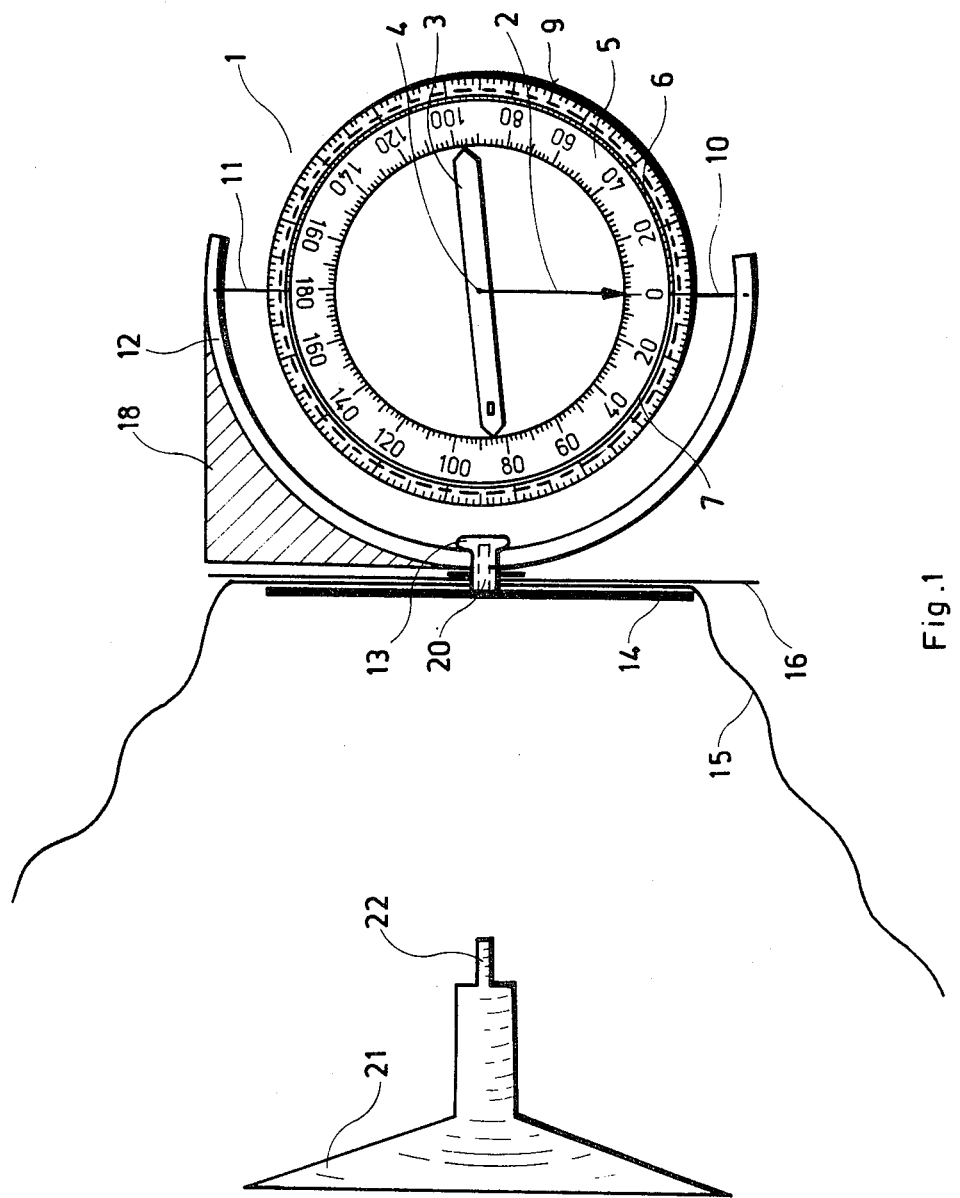
Figure 2:
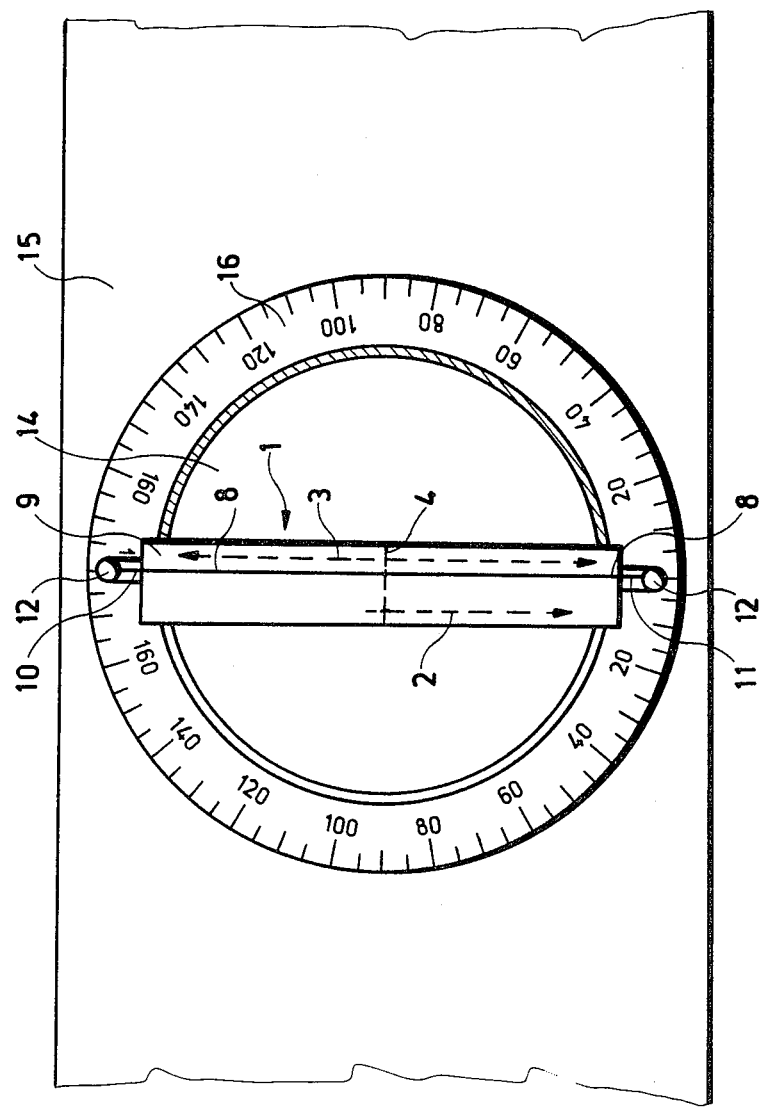
FIG. 2 is a plan view of the embodiment in FIG. 1.
Figure 3:
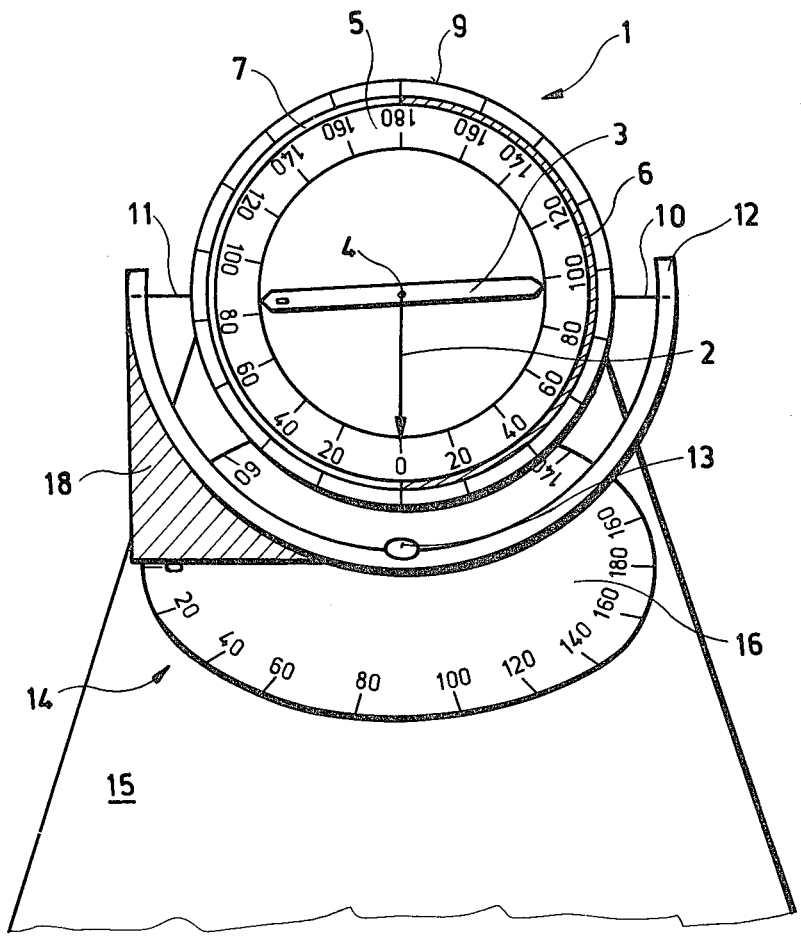
FIG. 3 is a perspective view of the embodiment shown in FIG. 1.

In FIGS. 1 to 3, an exemplified embodiment of the instrument of this invention is shown in various views. As is apparent, the basic unit of the instrument is a combined dip-circle (inclinometer) and compass shown by reference numeral 1. The dip-circle has a free moving pointer 2, thus, the pointer 2 will always point down if the dip-circle is in the vertical plane or near to it. The compass of unit 1 has a compass needle 3 pointing in the North-South direction in the roughly horizontal plane of the compass. Pointer 2 and compass needle 3 have a common axis of rotation 4. Thus, the same instrument can be used for measurements in the vertical plane as well as in the horizontal plain. A common angle calibration 5 is related to both dip-circle and compass of unit 1. The calibration 5 is formed as two mirror-image symmetrical semicircles 6 and 7 wherein both semicircles 6 and 7 have a calibration from 0 to 180 degrees. The semicircles 6 and 7 are differentiated by two colors, e.g. semicircle 6 is red, semicircle 7 is green.

The unit 1 with dip-circle and compass as well as angle calibration 5 are built into a common housing 9. Relative to this housing 9, the angle calibration 5 can be revolved at 8. The housing 9 is pivotally joined to arms of a bifurcated holder 12 by axle pins 10 and 11 fixed in the arms of the holder 12. Axle pins 10 and 11 lie on a common line which is perpendicular to axis of rotation 4 of pointer 2 and compass needle 3. Thus, the housing 9 can freely be rotated between the arms of the holder 12 but it remains in its position into which it is set. For this purpose, for example, the pins 10 and 11 are fitted tightly in housing 9.

The bifurcated holder 12 is pivotedly jointed to a base plate 14 by an axle pin 13 which is perpendicular to base plate 14 as well as to axle pins 10 and 11 of bifurcated holder 12. Similarly to the joint of pins 10 and 11 in housing 9, the axle pin 13 is also tightly fitted in the bifurcated holder 12 for rotation but for remaining in its position into which it is set. With this arrangement, the combined unit 1 can be set into any optional position in space after fixing the instrument of this invention on the patient.

On the base plate 14, a rubber belt 15 is fixed for securing the instrument on the object to be examined. Also, an angle calibration 16 is fixed on the base plate for reading off the rotation of the bifurcated holder 12 relative to the base plate 14. The angle calibration 16 is formed as two mirror-image symmetrical semicircles each having a calibration of 0 to 180 degrees. The line interconnecting the points of 0 degree and 180 degrees is perpendicular to the longitudinal axis of the rubber belt 15. The semicircles of angle calibration 16 are differentiated by different colors, e.g. the one is red, the other is green.

The bifurcated holder 12 has a pointing edge 18 which is formed as an elongation of the middle plane of the holder 12. The pointing edge 18 is related to angle calibration 16, i.e. it rotates closely above the calibration 16 together with holder 12. Thus it displays the rotation of the bifurcated holder 12.

To the base plate 14, a sucker 21 is attached on its side opposite the bifurcated holder 12 for preventing the displacement of the instrument on the object to be measured. For this purpose, a central opening 20 is provided in base plate 14 in which a central pin 22 of the sucker 21 is connected, e.g. by way of a detachable connection.

The plane defined by the periphery of the sucker 21 or its middle plane is parallel to the base plate 14. Central pin 22 of the sucker 21 can have various lengths for various fields of examination. Sometimes, the instrument fixed on the patient can get in the way of the movement of the examined object. Therefore, an extension bar (not shown) can be detachably provided between the central pin 22 of the sucker 21 and the central opening 20 of the base plate 14. The length of the extension bar can be adjustable for various examination purposes.

The function of the instrument of this invention as shown in FIGS. 1 to 3 will be described hereinafter with reference to the further figures. As is apparent, the axis of rotation formed by axle pins 10 and 11 is always parallel to base plate 14, thus, the position of this axis of rotation can directly be read off the angle calibration 5 of unit 1, e.g. on its outer periphery. Furthermore, this value gives the position of the base plate 14 relative to the vertical (dip-circle) or to the North-South direction (compass).

In the examination of organs of the locomotion system, the measurements should preferably have an accuracy of 5 degrees. In some special fields of examination, e.g. the spinal column, an accuracy of 2 to 3 degrees is desirable because of the diagnostical consequences, on one hand, and of the evaluation of various therapies, on the other.

Figure 4:
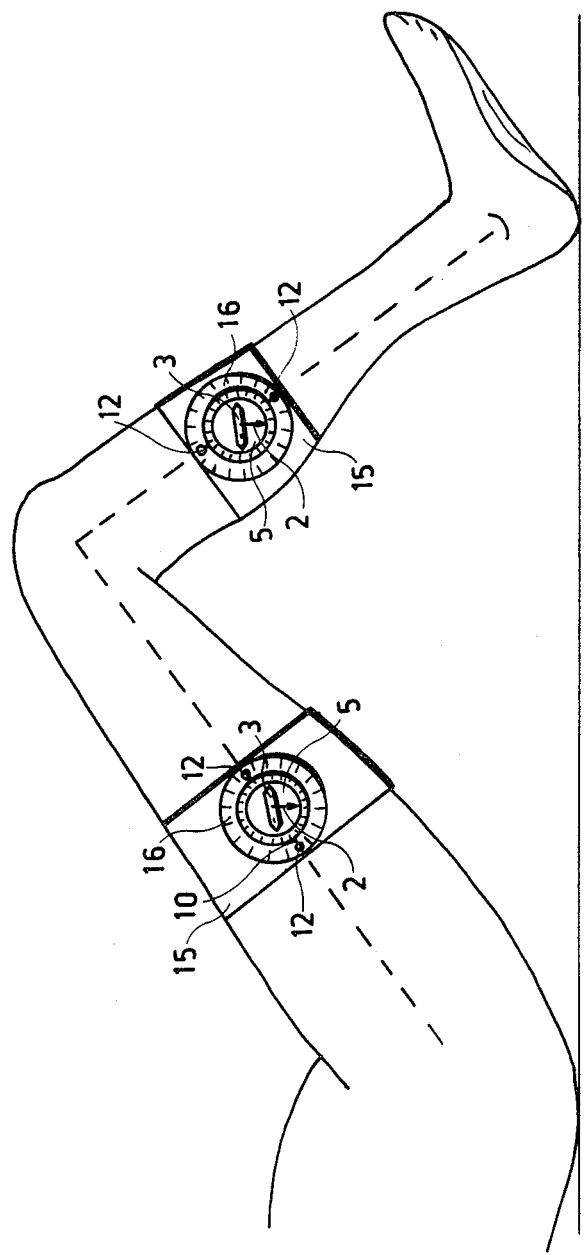
FIG. 4 shows the examination of the knee joint and the hip joint with an embodiment of the instrument of this invention.

In FIG. 4, a lower extremity of a patient is shown in a position of examination. Middle axes of the thigh and the shin are shown by dashed lines. When measuring, it is important that the extremities have a roughly cylindrical or conical shape and the axes shown with dashed lines are their middle or symmetry axes. The instruments are fixed on the extremities with the rubber belt 15 which is roughly perpendicular to the axis of the extremity. Thus, a line interconnecting the point of 0 degrees and the point of 180 degree of angle calibration 16 of the base plate 14 is parallel to the axis of the extremity.

The examination is carried out as follows: Referring to FIG. 4, the hip joint is measured by an instrument of this invention fixed on the thigh. According to the up-to-date method of neutral zero, the initial, i.e. neutral or zero position of the hip joint is that in which the thigh is entirely stretched out. In this examination, the dip-circle (inclinometer) of unit 1 is used, i.e. the inclination in the vertical plane is measured. For this, 0 degree on the angle calibration 5 of unit 1 is rotated to the pointer 2 of the dip-circle in the initial stretched out position of the thigh. Thereafter, the thigh is bent to its other final position wherein the angle value shown by pointer 2 on angle calibration 5 is read off. This angle value gives directly the flexure of the hip joint.

Let us suppose, that the patient is not healthy, he has a so called flexure contraction of the hip joint, i.e. he cannot stretch entirely his thigh, thus, the neutral position cannot be reached. In this position of the thigh stretched as far as possible, the pointing edge 18 of the bifurcated holder 12 is rotated to 0 degree on the angle calibration 16 of the base plate 14. As a result of this the line of axle pins 10 and 11 will be parallel to the middle axis of the thigh. The dip-circle will be adjusted to 0 by rotating the angle calibration 5 to the pointer 2 and the angle value shown at the axle pin 10 on the outer periphery of the angle calibration 5 is read off. After subtracting this value from 90 degrees, the value angle of the contraction is given, since the angle between the healthy (entirely stretched) thigh and the vertical is 90 degrees.

For examining the knee joint, another instrument is fixed on the shin, too, as shown in FIG. 4. If the knee joint of an ill patient has a flexion contracture, the angles between the vertical and the middle axes of the thigh and the shin are to be measured. For this, the instruments are adjusted to zero as described above in connection with the hip joint (pointing edge 18 to 0 on angle calibration 16, 0 of angle calibration 5 to pointer 2 of dip-circle). The values are read off the outer periphery of angle calibration 5. The sum of these angles gives the contracture of the knee joint.

In this measurement, the different colors of the semicircles of angle calibration 5 play a role. As will be apparent, it is a general rule with this instrument that if the angles are shown in semicircles having different colors they are added but by contrast if they are shown in semicircles having the same color, they are substracted.

For measuring the rotation of the knee joint, only one instrument might be sufficient if the thigh is fixed and has not any displacement during the examination. With two instruments fixed as shown in FIG. 4, also the thigh may move. The instruments are adjusted to zero as described above and the values read off angle calibrations 5 of the instruments are added or subtracted depending on the colors of the semicircles at the pointers 2.

In practice, the abduction of the hip joints are to be measured, too, which are the moving off and the approaching the middle line of the body by the thigh. Unit 1 is adjusted into a plane parallel to the so-called frontal plane of the body. This can easily be done since unit 1 can be set in an optional position in space because of the axis of rotation at axis 4, at axle pins 10 and 11, and at axle pin 13 each being perpendicular to the other in the space. The instrument is fixed to the thigh and adjusted to 0 in the neutral position of the hip joint. Thereafter, the angle values corresponding to the maximum abduction can directly be read off the angle calibration 5.

Figure 5:
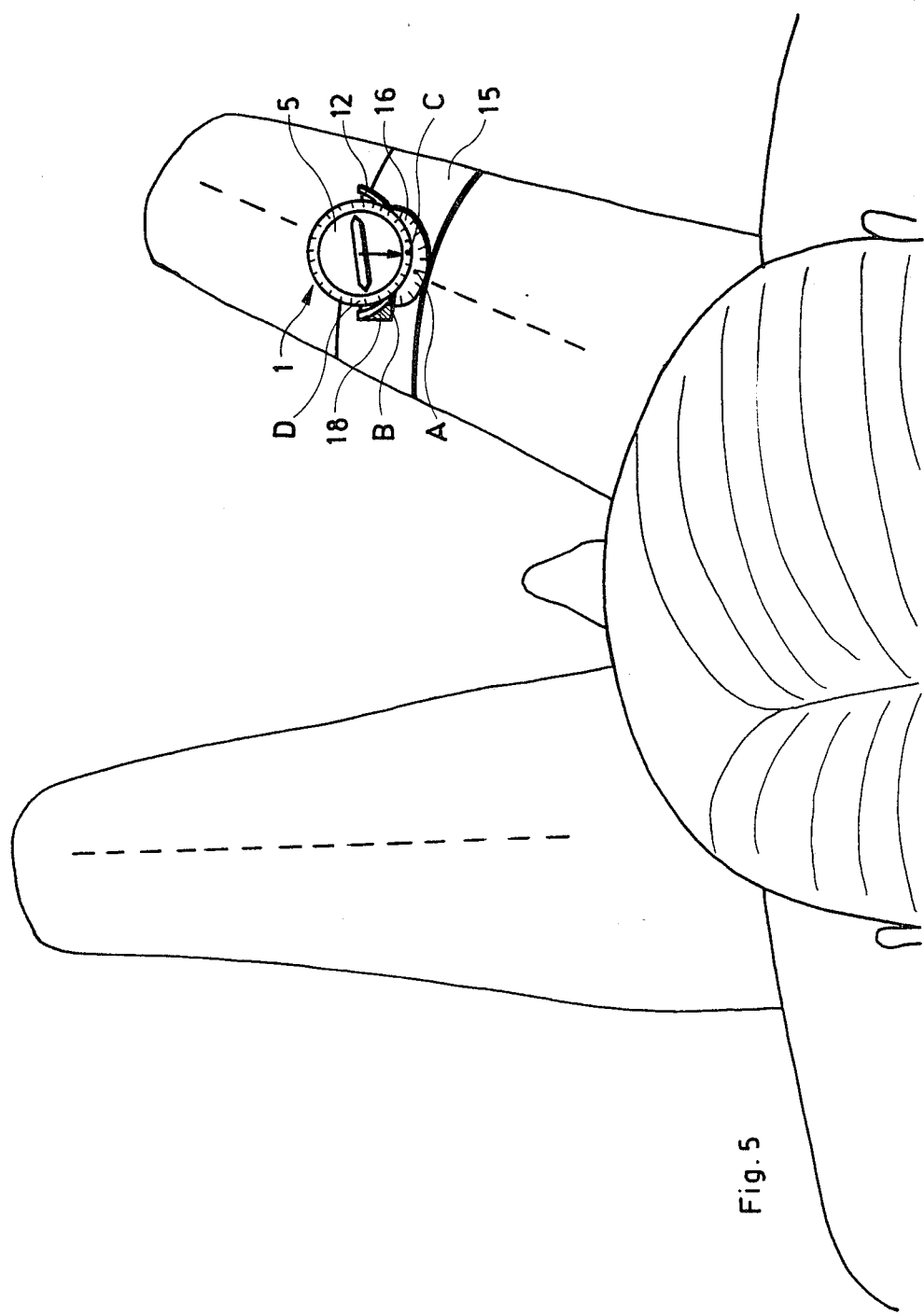
FIG. 5 shows the examination of the hip joint of another patient.

For measuring the rotation of the hip joint, the compass of unit 1 is used as is illustrated in FIG. 5. The unit 1 is rotated into the horizontal plane and is adjusted to zero by rotating angle calibration 5 to compass needle 3 in the neutral position of the hip joint. After rotating the thigh outwards and inwards, the angle values are read off the angle calibration 5 at compass needle 3. If the unit 1 is not longer in the horizontal plane at the end of rotation, this can be corrected without difficulty which is necessary for the precise measuring with the compass.

The angle calibration 16 is used with more contractions limiting the ability of movement in one joint. The contraction in abduction as well as the abduction can be measured with an accuracy of 1 degree by fixing the instrument on the frontal surface of the thigh. Unit 1 is positioned in the frontal plane for which pointing edge 18 is rotated away from 0 on angle calibration 16. However, the line interconnecting 0 degrees and 180 degrees is still parallel to the middle axis of the thigh. The pointer 2 of the dip-circle in the frontal plane, is set to 0 of the angle calibration 5. Thus, the difference of angle AB (FIG. 5) on the angle calibration 16 of base plate 14 and of the angle CD read off the angle calibration 5 at axle pin 11 gives the angle value between the axis of the thigh and the vertical, i.e. the exact value of the contracture in abduction of the hip joint. Also in this case, the values read off semicircles having the same color are to be subtracted.

Figure 6:
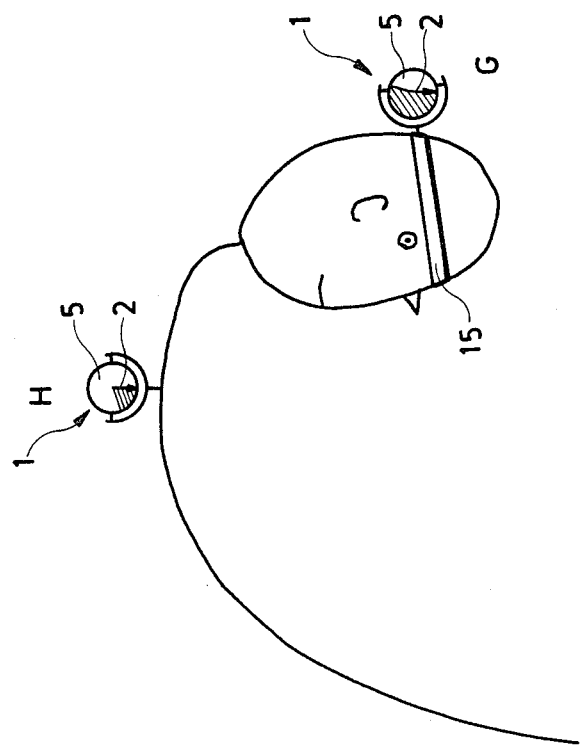
FIG. 6 illustrates the examination of the neck with the instrument of this invention.
Figure 6:
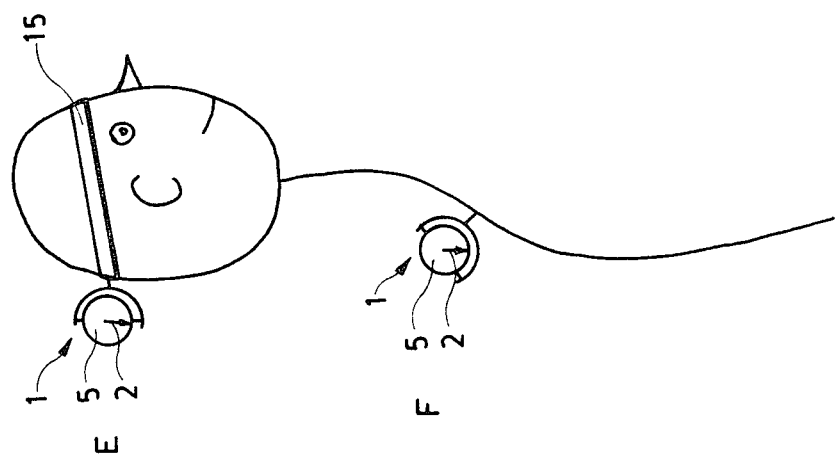
Figure 7:
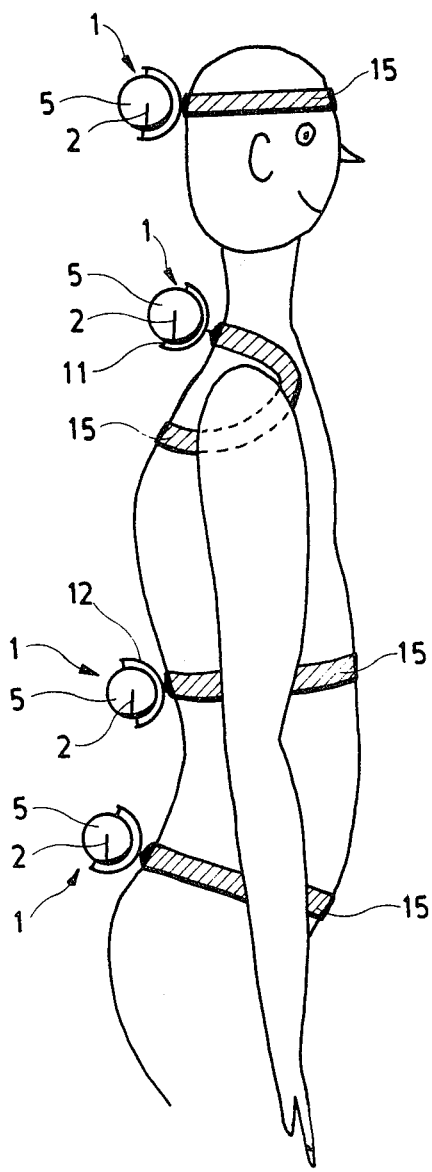
FIG. 7 is a side view of an examination configuration with the instrument of this invention.

As was described above in detail, the problem of measuring the positions and displacements of the spinal column was not solved by the prior art. The principle of the measuring is shown in FIG. 6, wherein the examination of the cervical spine is illustrated. At the end points of this part of the spine, an instrument according to this invention is fixed, that is on the head of the patient and above the seventh cervical vertebra spondyle. For this measurement, the dip-circle of unit 1 is used and the unit 1 is set into a plane which is perpendicular to the frontal plane and is vertical. The instruments are set to zero by rotating 0 of angle calibrations 5 to pointers 2 in the neutral position of the spinal column. After bending forward, the pointers 1 enfilade the angle fields of angle calibrations 5 as shown by shade-lines in the FIG. 6. With the instrument shown by H in FIG. 6, the displacement of the trunk, with the instrument G, the displacements both of the trunk and the neck together are shown. The difference of these two values gives the exact angle of flexure of the cervical spine.

With the same arrangement, the extension (leaning backward) of the cervical spine can be measured, too.

The bending sidewards of the spine (to the left and to the right) is measured with the instruments set in a plane parallel to the frontal plane.

The rotation of this part of the spinal column is measured with the compass needle 3 and, thus, with instruments set in the horizontal plane.

With four instruments of this invention, all three parts of the spinal column: the cervical, the dorsal and the lumbar one can be measured separately, independently or in any combination. The instruments are secured on the body with rubber belts 15. The bottom instrument is fixed on the surface of the sacrum which is tightly connected to other parts of the pelvis, thus, the movements of the hip joint can be subtracted from the angle value measured with the instrument fixed on the last dorsal vertebra spondyle. In this way, the displacements falsifying the measurements can be eliminated.

As is stated above, not only the displacements but the positions, static shape, and existing curvatures of the spinal column can be measured, too. This is made possible with the line of axle pins 10 and 11 being always parallel to the base plate 14. Going back to FIG. 6, the base plate 14 of the instrument shown at F and lying against the last cervical vertebra spondyle is parallel to axle pin 10. After adjusting 0 of angle calibration 5 to the pointer 2 of the dip-circle, the angle value between the vertical and the bottom part of the cervical spine can be read off the angle calibration 5 at axle pin 10.

Figure 8:
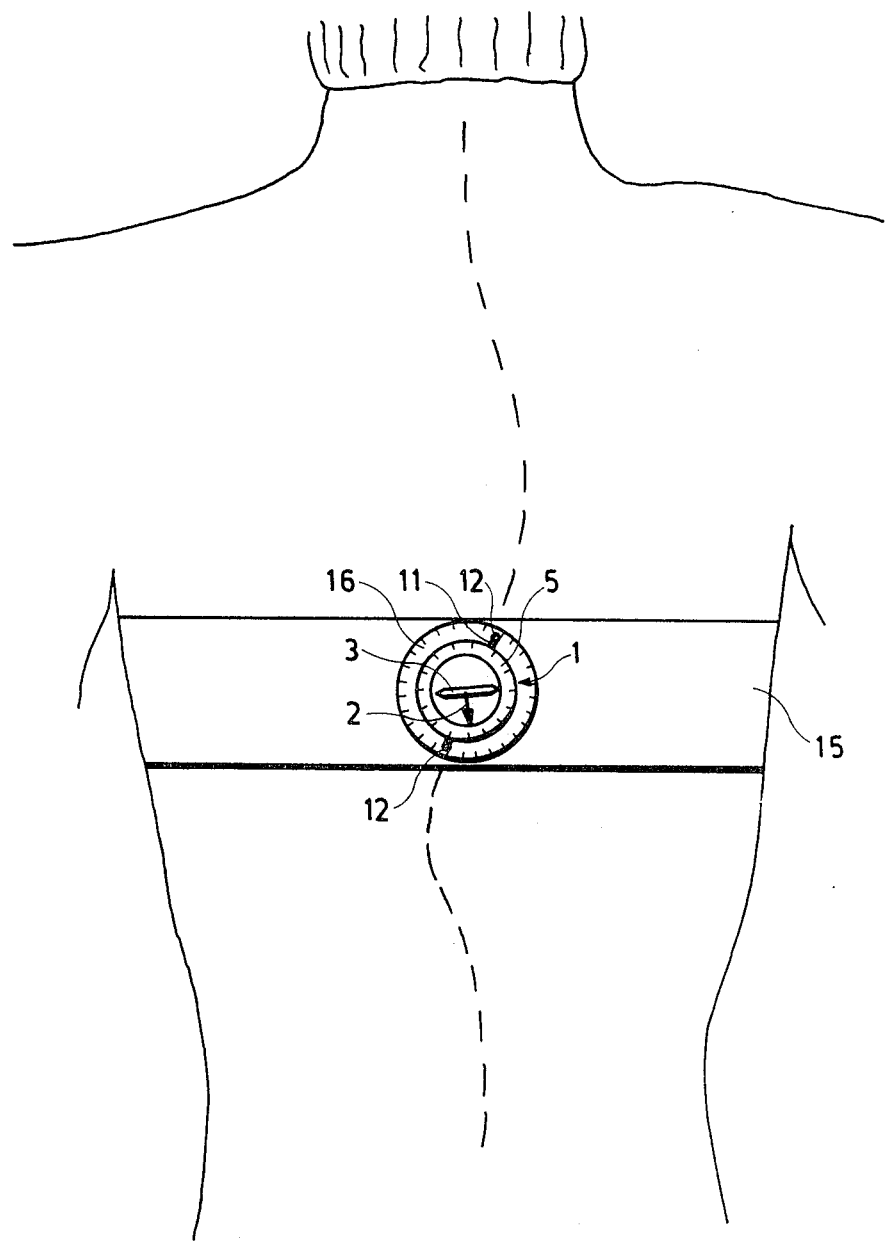
FIG. 8 shows a backbone examination with the instrument of this invention.

In FIG. 8, the sidewards curvature (scoliosis) of the spinal column is illustrated. After securing the instrument with rubber belt 15 at the portion of the spine to be measured, pointing edge 18 of bifurcated holder 12 is rotated into alignement with the curved spinal part. The angle of the curved part to the vertical can be read off the calibration 16 of base plate 14 at pointing edge 18 or an angle calibration 5 of the dip-circle in unit 1 being in a plane parallel to the frontal plane.

For measuring the leaning forward or backward of the spine (kyphosis or lordosis), the pointing edge 18 is set to 0 on angle calibration 16, 0 of angle calibration 5 of unit 1 is set to axle pin 10 and unit 1 is rotated into a plane perpendicular to the frontal plane. In the case of kyphosis, the measured angle value read off angle calibration 5 at pointer 2 of the dip-circle has a positive value, whereas in the case of lordosis, this value is negative.

Figure 9:
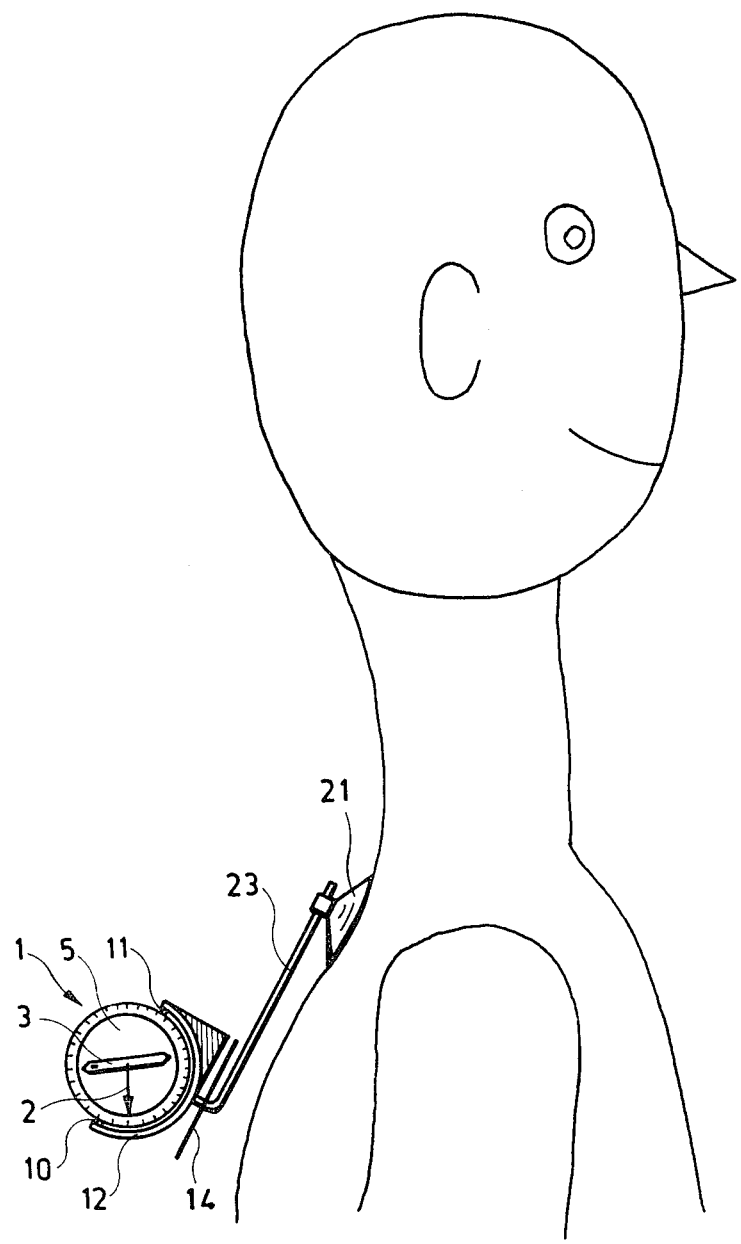
FIG. 9 illustrates another embodiment of the instrument of this invention fixed on the neck of a patient.

In some cases, the instrument fixed on the body may be in the way of movement. The instrument secured on the seventh cervical vertebra spondyle, for example, may collide with the head bent entirely back. For preventing this, an extension bar (not shown) can be inserted between sucker 21 and base plate 14 as is shown in FIG. 9. The extension bar has an adjustable length and is parallel to base plate 14 as well as to middle plane or plane of connection of sucker 21. Thus, inserting an extension bar does not affect the measuring.

The instrument of this invention may have a very manifold application in the medical sciences, in the clinical praxis of rheumatics, orthopedy, traumatology and rehabilitation of the locomotion system. The spondylearthritis ankylopoetica can be recognized in an early state by measuring whether the rotation and bending sidewards of the spinal column progressively decrease. In forensic medicine, the state of the organs of locomotion can be measured objectively. By detecting that the displacement of the spinal column is smaller and asymmetrical, idiopathic scoliosis can be recognized in an early stage. Furthermore, new therapeutical methods can exactly be evaluated and controlled by precise measurements with the instrument of this invention.

We claim:

1. An instrument for measuring positions and displacements of portions of a human body, comprising a base plate, means for detachably securing the base plate to a portion of a human body, a holder mounted on the base plate rotatably about a first axis, said holder having a pair of arms, a housing pivotally carried between said arms rotatably about a second axis perpendicular to said first axis, a dip circle having a pointer and means for causing the circle to align the pointer to point vertically downward under the influence of gravity, a north-south-seeking compass carried by said housing, said dip circle and compass being rotatably mounted on said housing about a common third axis perpendicular to said second axis, one of said base plate and said holder having a scale thereon, indicator means on the other of said base plate and said holder for indicating on said scale the angular position of said holder relative to said base plate, and scale means on said housing for indicating the angular position of said dip circle and said compass relative to said housing.

2. An instrument as claimed in claim 1, said scale extending to 180° of arc in opposite directions from a zero mark.

3. An instrument as claimed in claim 1, said scale means on said housing extending to 180° of arc in opposite directions from a 0 mark on said housing.

4. An instrument as claimed in claim 1, said securing means comprising a flexible belt, a line connecting 180° on said scale and said zero mark on said scale being perpendicular to the length of said belt.

5. An instrument as claimed in claim 1, said securing means comprising a suction cup.

6. An instrument as claimed in claim 1, and means for rotating said scale means relative to said housing about said common third axis.

* * * * *